(12) United States Patent
Chang et al.

(10) Patent No.: US 8,003,272 B2
(45) Date of Patent: Aug. 23, 2011

(54) FUEL CELL FOR MICROCAPSULE-TYPE ROBOT AND MICROCAPSULE-TYPE ROBOT POWERED BY THE SAME

(75) Inventors: Hyuk Chang, Seongnam-si (KR); Kyoung Hwan Choi, Suwon-si (KR); Christopher Hansung Ko, Seongnam-si (KR)

(73) Assignee: Samsung SDI Co., Ltd., Suwon (KR)

( * ) Notice: Subject to any disclaimer, the term of this patent is extended or adjusted under 35 U.S.C. 154(b) by 1101 days.

(21) Appl. No.: 11/262,813

(22) Filed: Nov. 1, 2005

(65) Prior Publication Data

US 2006/0094928 A1    May 4, 2006

(30) Foreign Application Priority Data

Nov. 2, 2004    (KR) .................. 10-2004-0088164

(51) Int. Cl.
*H01M 8/24*    (2006.01)
(52) U.S. Cl. ......... 429/466; 429/463; 429/505; 429/506
(58) Field of Classification Search ............ 429/29, 429/40, 466
See application file for complete search history.

(56) References Cited

U.S. PATENT DOCUMENTS

| | | | | |
|---|---|---|---|---|
| 4,294,891 A | * | 10/1981 | Yao et al. | 429/2 |
| 4,810,596 A | * | 3/1989 | Ludwig | 429/17 |
| 2001/0050234 A1 | * | 12/2001 | Shiepe | 205/629 |
| 2002/0009626 A1 | * | 1/2002 | Terazono et al. | 429/30 |
| 2002/0076602 A1 | * | 6/2002 | Finkelshtain et al. | 429/40 |
| 2003/0027032 A1 | * | 2/2003 | Sugita et al. | 429/35 |
| 2003/0214580 A1 | * | 11/2003 | Iddan | 348/81 |
| 2004/0072044 A1 | * | 4/2004 | Rusek et al. | 429/30 |

FOREIGN PATENT DOCUMENTS

KR    10-2004-0055293    6/2004

* cited by examiner

*Primary Examiner* — Ula C Ruddock
*Assistant Examiner* — Patricia Davis
(74) *Attorney, Agent, or Firm* — H.C. Park & Associates, PLC

(57) ABSTRACT

A fuel cell for a microcapsule-type robot uses alcohol or an aqueous alcohol solution as a fuel and was hydrogen peroxide or an aqueous hydrogen peroxide solution as an oxidizing agent. A microcapsule-type robot also uses the fuel cell. The fuel cell may be used in a microcapsule-type endoscope and have an operating time that is long enough to diagnose human organs. The fuel cell may comprise hydrogen peroxide as an oxidizing agent instead of air or oxygen such that the fuel cell can operate inside the human body. Thus, an oxygen source, which cannot be obtained in a human body, can be easily supplied to the fuel cell, and the fuel cell has higher performance than a fuel cell in which air is used as an oxidizing agent.

13 Claims, 4 Drawing Sheets

FUEL CELL FOR MICROCAPSULE-TYPE ROBOT AND MICROCAPSULE-TYPE ROBOT POWERED BY THE SAME

CROSS-REFERENCE TO RELATED APPLICATION

This application claims priority to and the benefit of Korean Patent Application No. 10-2004-0088164, filed on Nov. 2, 2004, in the Korean Intellectual Property Office, the disclosure of which is incorporated herein in its entirety by reference.

BACKGROUND OF THE INVENTION

1. Field of the Invention

The present invention relates to a fuel cell for a microcapsule-type robot and a microcapsule-type robot that uses the fuel cell. In particular, the present invention relates to a fuel cell for a microcapsule-type robot in which alcohol or an aqueous alcohol solution is used as a fuel and hydrogen peroxide or an aqueous hydrogen peroxide solution is used as an oxidizing agent, and a microcapsule-type robot that uses the fuel cell.

2. Description of the Background

An endoscope is widely used to examine or treat lesions of the internal organs in a human body without performing surgery that incises the skin. However, when patients are examined or diagnosed using a cable endoscope, they may experience pain and discomfort, and thus, these procedures have not been welcomed by patients. This owes primarily to the significant size of the endoscope itself and the sensation of a wire that supplies power to the endoscope. Recently, patients are subjected to a general anesthetic so that they can avoid these discomforts and pain. However, the use of such a general anesthetic can be dangerous, so endoscopy with anesthesia is typically avoided.

In order to overcome these problems, indirect procedures including virtual colonoscopy and gene examination methods have been developed. However, a doctor cannot directly observe and treat an affected part or perform a biopsy, etc.

In order to overcome the above problem, a microcapsule-type endoscope has been developed in which a unit that photographs and transmits images is installed in a swallow-able capsule. When a patient swallows the microcapsule-type endoscope, the endoscope travels along the digestive organs while obtaining image information from the organs and transmits the image information to a receiving unit outside the patient's body. The receiving unit interprets the received image information which is used to diagnose the condition of the patient's organs. The conventional cable endoscope can diagnose only the large intestine or stomach, but the conventional microcapsule-type endoscope can diagnose the small intestine in addition to the large intestine and stomach. Thus, the microcapsule-type endoscope provides a wider range of medical diagnosis.

A mercury oxide ($HgO_2$) cell that uses mercury is used as a power supply for the microcapsule-type endoscope. When the sheathing of the microcapsule-type endoscope is damaged due to gastric acids and various enzymes in the human body and other unexpected chemical reactions of digested foods, etc., there is a risk that the body will be exposed to the mercury. In addition, the mercury oxide cell has a short operating time of 4-6 hours, so while it passes through the small intestine, the power may be exhausted and thus the large and small intestines cannot be diagnosed at the same time.

A microcapsule-type endoscope that is equipped with a pose control and/or a location control unit has been developed (Korean Patent Application No. 10-2002-81935), but such an endoscope consumes more power than a conventional microcapsule-type endoscope that does not have the pose or location control unit. Thus, there is an increasing need to develop a power supply that has a larger capacity for use in a microcapsule-type endoscope.

SUMMARY OF THE INVENTION

The present invention provides a fuel cell for a microcapsule-type robot that has high energy density which allows it to supply power for an extended time and is harmless to a human body.

The present invention also provides a microcapsule-type robot that uses the fuel cell and has an extended operating time.

Additional features of the invention will be set forth in the description which follows, and in part will be apparent from the description, or may be learned by practice of the invention.

The present invention discloses a fuel cell for a microcapsule-type robot comprising a cathode to which a fuel is supplied, an anode to which an oxidizing agent is supplied, and an electrolyte membrane interposed between the cathode and the anode. The fuel is alcohol or an aqueous alcohol solution and the oxidizing agent is hydrogen peroxide or an aqueous hydrogen peroxide solution.

The present invention also discloses a microcapsule-type robot that uses the fuel cell as a power supply.

It is to be understood that both the foregoing general description and the following detailed description are exemplary and explanatory and are intended to provide further explanation of the invention as claimed.

BRIEF DESCRIPTION OF THE DRAWINGS

The accompanying drawings, which are included to provide a further understanding of the invention and are incorporated in and constitute a part of this specification, illustrate embodiments of the invention, and together with the description serve to explain the principles of the invention.

DETAILED DESCRIPTION OF THE ILLUSTRATED EMBODIMENTS

Figure 1:
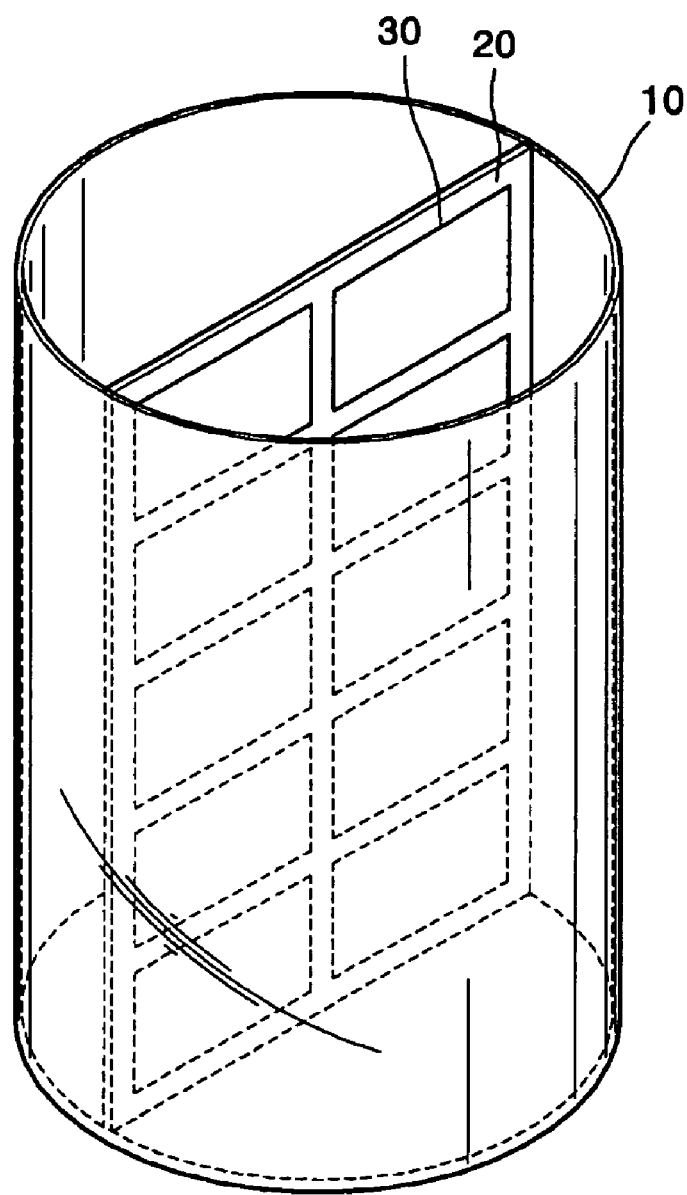
FIG. 1 is a schematic view of a fuel cell for a microcapsule-type robot according to an exemplary embodiment of the present invention.

The invention is described more fully hereinafter with reference to the accompanying drawings, in which embodiments of the invention are shown. This invention may, however, be embodied in many different forms and should not be construed as limited to the embodiments set forth herein. Rather, these embodiments are provided so that this disclosure is thorough, and will fully convey the scope of the invention to those skilled in the art. In the drawings, the size and relative sizes of layers and regions may be exaggerated for clarity.

It will be understood that when an element such as a layer, film, region or substrate is referred to as being "on" another element, it can be directly on the other element or intervening elements may also be present. In contrast, when an element is referred to as being "directly on" another element, there are no intervening elements present.

The term "robot" typically refers to an automated device that performs functions that are assigned to humans or a machine having a human-like shape. In this specification, however, the term "robot" refers to an automated device performs functions that are ordered by humans.

A fuel cell prepared according to the present invention may be used in a microcapsule-type endoscope to ensure an operating time that is long enough to diagnose human organs.

Further, the fuel cell according to the present invention includes hydrogen peroxide as an oxidizing agent instead of air or oxygen so that the fuel cell can operate inside the human body. Thus, an oxygen source, which cannot be obtained in the human body may be supplied easily to the fuel cell, and the fuel cell has better performance than a fuel cell in which air is used as an oxidizing agent.

Figure 2:
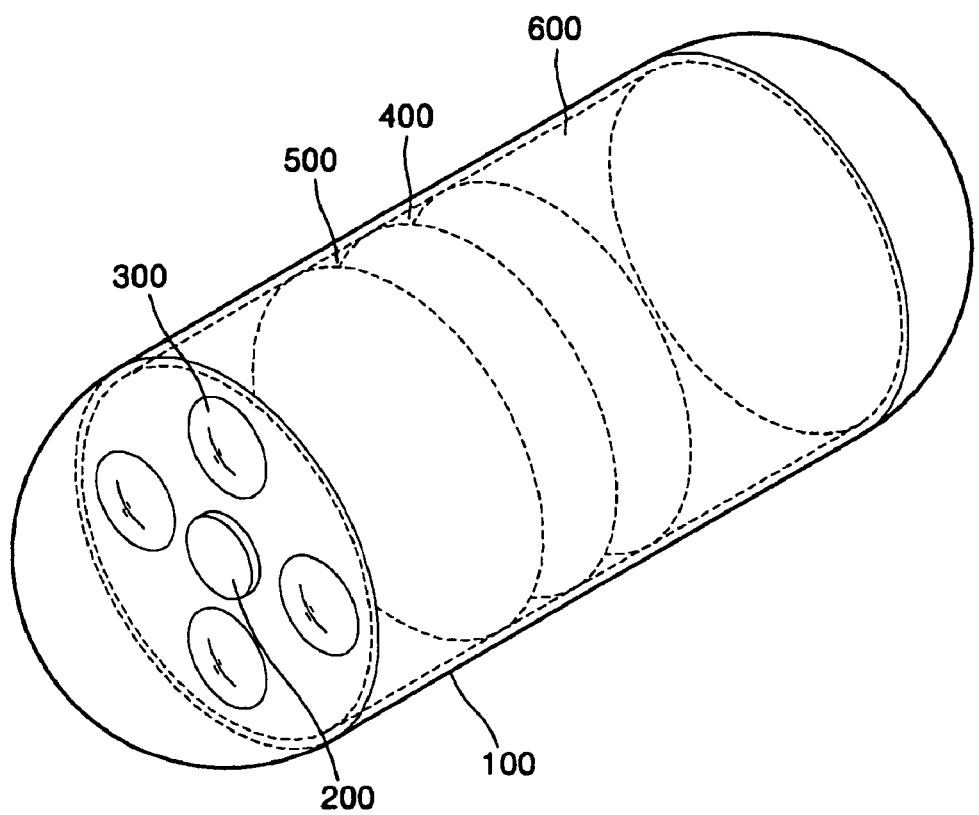
FIG. 2 is a schematic view of a microcapsule-type endoscope according to an exemplary embodiment of the present invention.

A microcapsule-type robot according to an exemplary embodiment of the present invention may be a microcapsule-type endoscope as illustrated in FIG. 2. The microcapsule-type endoscope comprises a capsule type robot body 100, a camera unit 200 located inside the capsule type robot body 100 to observe the internal organs of a human body, and a lighting unit 300 located inside the capsule type robot body 100 to irradiate light onto the internal organs such that the camera unit 200 can photograph the inside of the internal organs. In addition, the microcapsule-type endoscope includes a transmitter 400 that is located inside the capsule type robot body 100 to transmit image data obtained by the camera unit 200 to the outside of the human body and a control unit 500 that is located inside the capsule type robot body 100 to control the operations of the camera unit 200, the lighting unit 300, and the transmitter 400. The microcapsule-type endoscope also includes a power supply unit 600 that is located inside the capsule type robot body 100 to supply power to the camera unit 200, the lighting unit 300, the transmitter 400, and the control unit 500.

In an exemplary embodiment of the present invention, a fuel cell is used as a power supply for a microcapsule-type robot such as a microcapsule-type endoscope to extend its operating time.

As mentioned above, since a mercury oxide cell that is used as a power supply for a conventional microcapsule-type endoscope has a short operating time, there is a limit on the range of diagnosis. In order to increase the operating time, a power supply with a high energy density must be used. A fuel cell according to an embodiment of the present invention has a high enough energy density to be used as the power supply for a microcapsule-type endoscope.

In order to use a fuel cell in a microcapsule-type endoscope, an oxidizing agent such as air or oxygen must be supplied. In a conventional fuel cell, a liquid fuel is contained in the fuel cell and oxygen in air may be used as an oxidizing agent. As a result, a container, an apparatus, and equipment for accommodating the oxidizing agent are not required. Thus, the weight and volume of the fuel cell may be reduced. However, in a microcapsule-type endoscope that is to be used in a human body, oxygen is not present outside the fuel cell, and thus, the oxidizing agent must be provided in the fuel cell.

Methanol may be used as a fuel since it does not require a fuel reformer, is convenient to handle, and reduces the size of a fuel cell. According to an exemplary embodiment of the present invention, a direct methanol fuel cell (DMFC) is most suitable. The following reactions occur in the electrodes of the DMFC:

Scheme 1

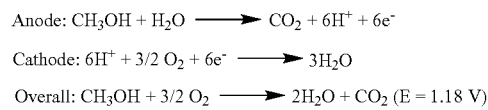

As described above, the oxidizing agent is also contained in the fuel cell according to an exemplary embodiment of the present invention. The oxidizing agent may be hydrogen peroxide or an aqueous hydrogen peroxide solution. Water may be supplied to the anode with methanol or some of the water generated at the cathode may be supplied to the anode and then used as a reactant at the anode.

A reduction reaction occurs at the cathode, which includes a catalyst for reducing hydrogen peroxide and a catalyst for reducing oxygen. These catalysts may be any workable metal catalysts that are used in manufacturing fuel cells. The catalyst for reducing hydrogen peroxide may be Al, Fe, Mn, etc. Pt may be used to reduce oxygen. In particular, these catalysts may be a Pt/Al catalyst. The Pt/Al catalyst may include double-layers comprising a Pt layer and an Al layer such that a first reduction reaction of hydrogen peroxide occurs in the Al layer and a second reduction reaction of oxygen occurs in the Pt layer. Alternatively, the Pt/Al catalyst may have only a single layer comprising a combination of Pt with Al such that the first reduction reaction of hydrogen peroxide and the second reduction reaction of oxygen occur simultaneously in the single layer.

The catalyst used in the anode may be any workable metal catalyst that is used in manufacturing a fuel cell. In particular, the catalyst may be a PtRu-based alloy.

The human body may be harmed with direct exposure to methanol. Thus, an alcohol which is not harmful to the human body may be used instead of methanol, such as inexpensive ethanol.

When ethanol is used in a fuel cell according to an exemplary embodiment of the present invention, the following reactions occur in the anode and the cathode:

Scheme 2

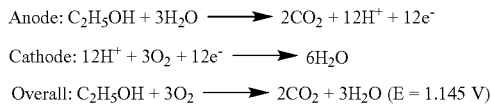

Similarly to when methanol is used as the fuel, the oxidizing agent may be hydrogen peroxide or an aqueous hydrogen peroxide solution when using ethanol as the fuel. Water may also be supplied to the anode along with ethanol or some of the water generated at the cathode may be supplied to the anode to be used as a reactant.

As when methanol is used as the fuel, the cathode's catalyst may be any workable metal catalyst that is used in manufacturing a fuel cell when using ethanol as the fuel. The catalyst for reducing hydrogen peroxide may be Al, Fe, Mn, etc. The catalyst for reducing oxygen may include Pt such as a Pt/Al catalyst.

The Pt/Al catalyst may be a double-layer comprising a Pt layer and an Al layer such that a first reduction reaction of hydrogen peroxide occurs in the Al layer and a second reduction reaction of oxygen occurs in the Pt layer. Alternatively, the Pt/Al catalyst may be a single-layer comprising a combination of Pt with Al such that the first reduction reaction of hydrogen peroxide and the second reduction reaction of oxygen simultaneously occur in one layer.

The catalyst used in the anode may be any workable metal catalyst that is used in manufacturing a fuel cell. For example, when ethanol is used as the fuel, the catalyst may be a PtSn-based alloy.

When the fuel cell is used in a microcapsule-type robot, the type or structure of the fuel cell is not specifically limited.

FIG. 1 is an enlarged view of the power supply unit 600 illustrated in FIG. 2.

As shown in FIG. 1, a fuel cell frame 10 may have a cylindrical shape and a membrane-electrode assembly (MEA) 20 that divides the fuel cell frame 10 along a longitudinal direction. The MEA 20 comprises an electrolyte membrane (not shown), an anode on one surface of the electrolyte membrane, and a cathode on the other surface of the electrolyte membrane. The anode comprises a catalytic layer including a PtRu-based alloy (when methanol is used as a fuel) or a PtSn-based alloy (when ethanol is used as a fuel) as a catalyst, and a supporting layer. The cathode comprises a catalyst layer 30 that is a double-layer including a Pt-containing layer and an Al-containing layer or a single-layer including a combination of Pt and Al, and a supporting layer.

A space in the fuel cell frame 10 on the anode side of the MEA 20 is filled with methanol or an aqueous methanol solution, or alternatively ethanol or an aqueous ethanol solution. A space on the cathode side is filled with hydrogen peroxide or an aqueous hydrogen peroxide solution. The concentration of the aqueous methanol or ethanol solution may be about 5 M to about 20 M.

In the fuel cell, a reduction reaction and an oxidation reaction occur at the cathode and the anode, respectively, thus generating water at the cathode and carbon dioxide at the anode. When the water is not removed, the concentration of the alcohol decreases, thereby reducing the reaction rate. When the carbon dioxide is not removed, mass transfer may be reduced, thereby reducing the energy efficiency of the fuel cell. Accordingly, a member for removing these products is required, thus the fuel cell may further include a discharge unit that discharges the carbon dioxide and water.

It is not necessary to discharge all of the water that is generated at the cathode. All or some of the water that is generated at the cathode may be cycled to the anode to participate in the reaction that occurs at the anode.

Hereinafter, the present invention will be described in more detail with reference to the following examples. However, these examples are given for the purpose of illustration and are not intended to limit the scope of the invention.

EXAMPLE 1

A fuel cell frame with a cylindrical shape with an internal radius of 5 mm and a height of 16 mm was prepared. A 10 mm wide, 16 mm long, and 0.4 mm thick MEA was closely adhered to the internal surfaces of the fuel cell frame such that the MEA extended along the central axis of the fuel cell frame. The portion of the fuel cell frame to which the MEA was attached was sealed such that a fuel or an oxidizing agent could not flow to the other side.

In the MEA, Nafion 117® (DuPont) was used as an electrolyte membrane, a PtRu catalytic layer was placed on a surface of the electrolyte membrane, and a Pt/Al catalytic layer was placed on the other surface using a hot pressing method. The hot pressing was performed at 125° C. under 80 atm for 90 seconds. The Pt/Al catalytic layer was formed by coating a Pt ink on the electrolyte membrane and then coating an Al ink on the coated Pt layer.

The Pt ink was obtained by mixing 0.8 g of Pt with 40 g of a 5 wt % Nafion® dispersion and adding 15 g of water and 60 g of glycerol to the resulting mixture.

10 M methanol was injected into the anode side space and hydrogen peroxide was injected into the cathode side space.

The resulting fuel cell had a power density of 40 mW/cm$^2$. For a capsule type endoscope, 20 mW at 3 V and an operating time of 10 hours were required, and thus, a total power of 200 mWh was required. Thus, a minimum required area of electrode was 0.5 cm$^2$. Ten electrodes each having an area of 5 mm$^2$ were used to construct the MEA illustrated in FIG. 1 and the performance of the fuel cell was tested at 50° C. to obtain a graph of current density vs. cell potential of the fuel cell, as illustrated in FIG. 3.

COMPARATIVE EXAMPLE 1

A fuel cell was manufactured in the same manner as in Example 1, except that air was injected into the cathode side space, instead of hydrogen peroxide and the performance of the fuel cell was tested. The results are shown in FIG. 3.

Figure 3:
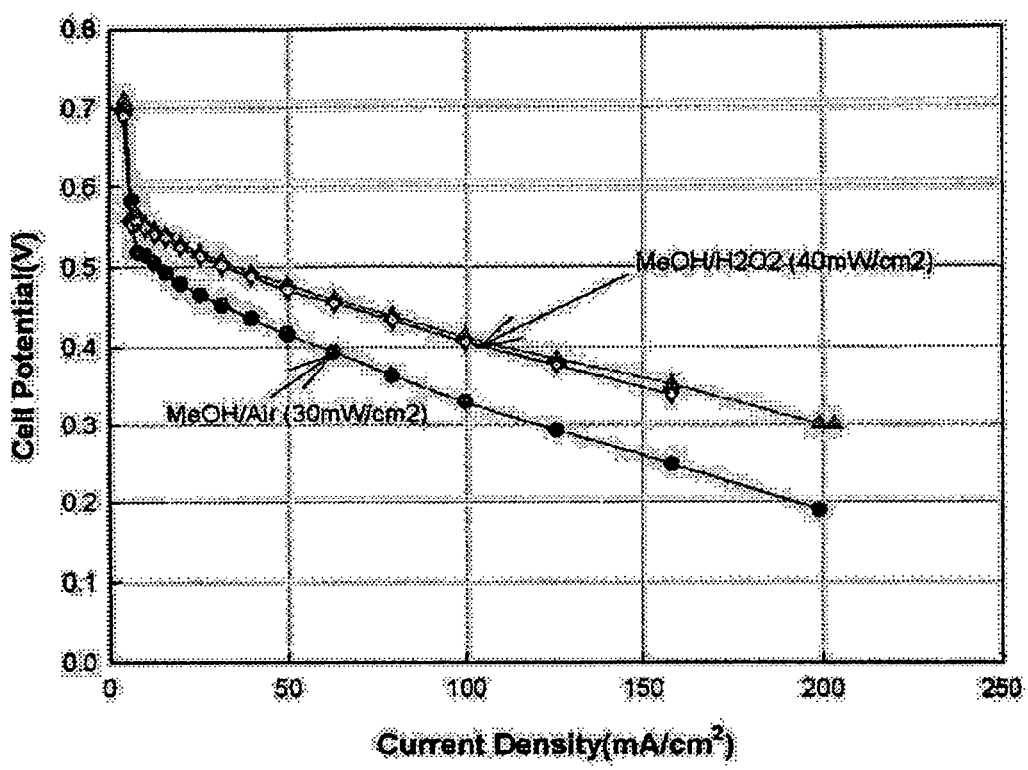
FIG. 3 illustrates graphs of current density vs. cell potential of fuel cells obtained in Example 1 and Comparative Example 1.

As shown in FIG. 3, the fuel cell obtained in Example 1 using hydrogen peroxide as the oxidizing agent had a higher cell potential than the fuel cell obtained in Comparative Example 1 using air as the oxidizing agent.

EXAMPLE 2

A fuel cell was prepared in the same manner as in Example 1, except that 10 M ethanol was used instead of 10 M methanol and a PtSn catalytic layer was used instead of the PtRu catalytic layer.

The resulting fuel cell had a power density of 20 mW/cm$^2$. The minimum area of the electrode was 1.0 cm$^2$ based on the required power. Ten electrodes each having an area of 10 mm$^2$ were used to construct the MEA illustrated in FIG. 1 and the performance of the fuel cell was tested at 50° C. to obtain a graph of current density vs. cell potential of the fuel cell, as illustrated in FIG. 4.

COMPARATIVE EXAMPLE 2

A fuel cell was prepared in the same manner as in Example 2, except that air was injected into the cathode side space instead of hydrogen peroxide. The results of the fuel cell's performance are shown in FIG. 4.

Figure 4:
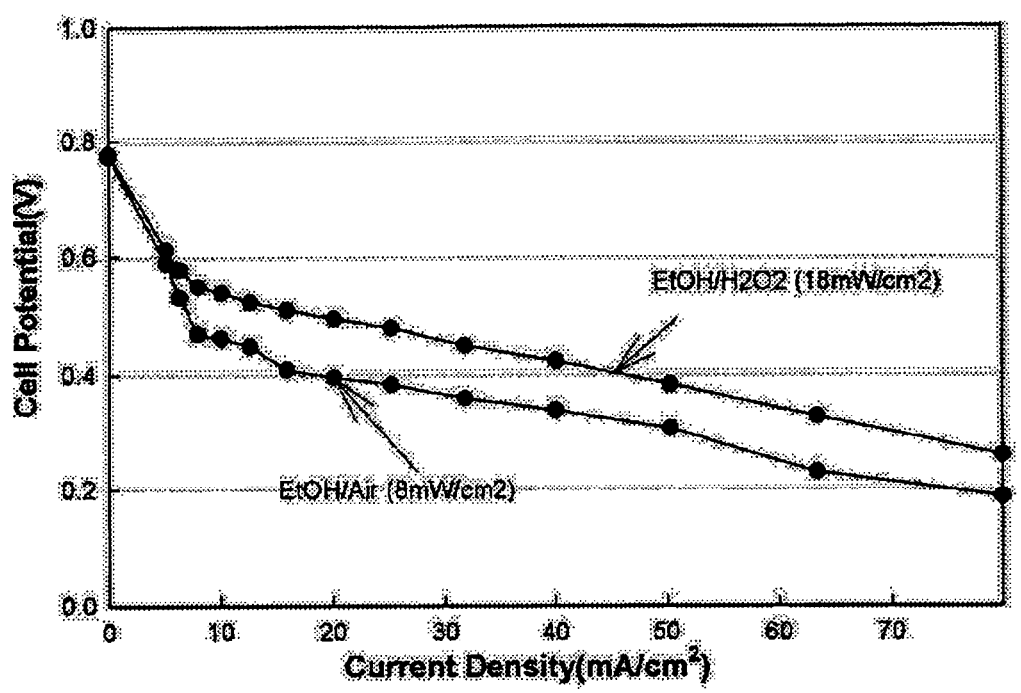
FIG. 4 illustrates graphs of current density vs. cell potential of fuel cells obtained in Example 2 and Comparative Example 2.

As shown in FIG. 4, the fuel cell obtained in Example 2 using hydrogen peroxide as the oxidizing agent had a higher cell potential than the fuel cell obtained in Comparative Example 2 using air as the oxidizing agent.

It will be apparent to those skilled in the art that various modifications and variation can be made in the present invention without departing from the spirit or scope of the invention. Thus, it is intended that the present invention cover the modifications and variations of this invention provided they come within the scope of the appended claims and their equivalents.

What is claimed is:

1. A fuel cell for a microcapsule-type robot, comprising:
a cylindrical fuel cell frame;
a cathode to which a fuel is supplied disposed in a region defined by the fuel cell frame;
an anode to which an oxidizing agent is supplied disposed in the region defined the fuel cell frame;
an electrolyte membrane interposed between the cathode and the anode, the electrolyte membrane dividing the region defined by the fuel cell frame into a cathode side corresponding to the cathode and an anode side corresponding to the anode;
alcohol or an aqueous alcohol solution disposed in a space on the anode side; and
hydrogen peroxide or an aqueous hydrogen peroxide solution disposed in a space on the cathode side,
wherein the fuel cell frame surrounds the space on the anode side and the space on the cathode side, and
wherein a first edge and a second edge of the electrolyte membrane contact the fuel cell frame to divide the fuel cell frame into the cathode side and the anode side.

2. The fuel cell of claim 1,
wherein the cathode comprises:
a catalytic double-layer comprising a first catalytic layer including Al and a second catalytic layer including Pt; or
a catalytic single-layer including Pt and Al.

3. The fuel cell of claim 1,
wherein the anode comprises a catalytic layer including a PtSn-based alloy or a PtRu-based alloy.

4. The fuel cell of claim 1,
wherein the alcohol or aqueous alcohol solution comprises ethanol or methanol.

5. The fuel cell of claim 1,
wherein the alcohol or aqueous alcohol solution comprises ethanol or an aqueous ethanol solution,
wherein the anode comprises a catalytic layer including a PtSn-based alloy, and
wherein the cathode comprises a catalytic double-layer including a first catalytic layer including Al and a second catalytic layer including Pt.

6. The fuel cell of claim 1,
wherein the alcohol or aqueous alcohol solution comprises methanol or an aqueous methanol solution,
wherein the anode comprises a catalytic layer including a PtRu-based alloy, and
wherein the cathode comprises a catalytic double-layer including a first catalytic layer including Al and a second catalytic layer including Pt.

7. The fuel cell of claim 1,
wherein all or some water that is generated at the cathode is supplied to the anode.

8. A microcapsule-type robot comprising the fuel cell of claim 1.

9. The microcapsule-type robot of claim 8,
wherein the microcapsule robot is a microcapsule-type endoscope, comprising:
a capsule type robot body;
a camera unit located inside the capsule type robot body;
a lighting unit located inside the capsule type robot body;
a transmitter located inside the capsule type robot body;
a control unit located inside the capsule type robot body to control the operations of the camera unit, the lighting unit, and the transmitter; and
a power supply unit positioned inside the capsule type robot body to supply power to the camera unit, the lighting unit, the transmitter, and the control unit.

10. The microcapsule-type robot of claim 8, further comprising:
a discharge unit that discharges carbon dioxide that is generated at the anode of the fuel cell and water that is generated at the cathode of the fuel cell.

11. The microcapsule-type robot of claim 10,
wherein all or some of the water that is generated at the cathode is supplied to the anode to participate in a reaction that occurs at the anode.

12. The fuel cell of claim 1,
wherein the electrolyte membrane divides the region defined by the fuel cell frame in a longitudinal direction.

13. The fuel cell of claim 1,
wherein the cathode side and the anode side are each arranged between the electrolyte membrane and the fuel cell frame.

* * * * *